United States Patent [19]

Tanno et al.

[11] 4,244,870

[45] Jan. 13, 1981

[54] DIMETHYL SULFOXIDE ADDUCTS OF PENICILLINS

[75] Inventors: Norihiko Tanno, Tokyo; Takashi Harimoto, Sonehigashi; Shinzi Ueda, Takarazuka; Hisao Tobiki, Kobe, all of Japan

[73] Assignee: Sumitomo Chemical Company, Limited, Osaka, Japan

[21] Appl. No.: 42,952

[22] Filed: May 29, 1979

[30] Foreign Application Priority Data

May 31, 1978 [JP] Japan ................................. 53/66144
May 31, 1978 [JP] Japan ................................. 53/66145

[51] Int. Cl.$^3$ .................. C07D 499/04; C07D 499/18; C07D 499/68
[52] U.S. Cl. ................................................ 260/239.1

[58] Field of Search ..................................... 260/239.1

[56] References Cited

U.S. PATENT DOCUMENTS 3,954,733  5/1976  Tobiki et al. ..................... 260/239.1

Primary Examiner—Natalie Trousof
Assistant Examiner—Vera C. Clarke
Attorney, Agent, or Firm—Birch, Stewart, Kolasch & Birch

[57] ABSTRACT

Sodium 6-[D(−)-α-(4-hydroxy-1,5-naphthyridine-3-carboxamido)phenylacetamido]penicillanate or its hydroxylated derivative at the p-position of the phenyl group in a crude state can be purified efficiently through its dimethyl sulfoxide adduct.

8 Claims, No Drawings

DIMETHYL SULFOXIDE ADDUCTS OF PENICILLINS

The present invention relates to the dimethyl sulfoxide adducts of sodium 6-[D(−)-α-(4-hydroxy-1,5-naphthyridine-3-carboxamido)phenylacetamido]penicillanate and of sodium 6-[D(−)-α-(4-hydroxy-1,5-naphthyridine-3-carboxamido)-p-hydroxyphenylacetamido]-penicillanate, and their production. It also relates to an industrial process for production of sodium 6-[D(−)-α-(4-hydroxy-1,5-naphthyridine-3-carboxamido)-phenylacetamido]penicillanate and of sodium 6-[D(−)-α-(4-hydroxy-1,5-naphthyridine-3-carboxamido)-p-hydroxyphenylacetamido]penicillanate of high purity.

6-[D(−)-α-(4-hydroxy-1,5-naphthyridine-3-carboxamido)phenylacetamido]penicillanic acid (hereinafter referred to as "Penicillin I") and 6-[D(−)-α-(4-hydroxy-1,5-naphthyridine-3-carboxamido)-p-hydroxyphenylacetamido]-penicillanic acid (hereinafter referred to as "Penicillin II") as well as their non-toxic salts are known to show a remarkable antimicrobial activity against Pseudomonas aeruginosa and exhibit a broader antimicrobial spectrum than ampicillin, amoxycillin, carbenicillin, sulbenicillin, etc. [cf. Japanese Patent Publication (examined) Nos. 17994/1975 and 17995/1975; Japanese Patent Publication (unexamined) No. 82683/1974].

The sodium salts of Penicillins I and II can be synthesized through coupling of ampicillin or amoxicillin with 4-hydroxy-1,5-naphthyridine-3-carboxylic acid according to a well known procedure in the peptide chemistry such as mixed acid-anhydride process, acid chloride process, active ester process or dicyclohexylcarbodiimide process. Under the reacting conditions as usually employed, however, there is produced a considerable amount (e.g. 3 to 10% by weight) of the decomposition by-product substance caused by cleavage of the β-lactam ring. When the once purified product is stored at room temperature for a long period, there is a tendency for the contaminating decomposition substance caused by cleavage of the β-lactam to increase. Further, the coupling of 6-aminopenicillanic acid with α-(4-hydroxy-1,5-naphthyridine-3-carboxamido)phenylacetic acid or α-(4-hydroxy-1,5-naphthyridine-3-carboxamido)-p-hydroxyphenylacetic acid according to a well known procedure in the peptide chemistry affords Penicillin I or II, which is contaminated with its L-isomer.

Elimination of the β-lactam ring cleaved decomposition substance and/or the steric isomer as stated above is extremely difficult. When any purification procedure, as conventionally adopted in the organic chemistyr, is applied the contaminating amount of the decomposition substance is increased due to the unstability of the β-lactam ring.

As a result of the extensive study for efficient elimination of the impurities without cleavage of the β-lactam ring, it has been found that the purification through the dimethyl sulfoxide adduct of the sodium salt of Penicillin I or II can achieve such elimination. Namely, the sodium salt of Penicillin I or II can easily form an adduct with dimethyl sulfoxide, which is highly crystallizable, while the impurities contaminating Penicillin I or II do not easily form such an adduct. Further, the formed adduct can be readily decomposed by treatment with a hydrous medium to liberate the sodium salt of Penicillin I or II and dimethyl sulfoxide. Moreover, the adduct is quite stable on storage and therefore very convenient for handling. The present invention is based on these findings.

According to the present invention, the sodium salt of Penicillin I or II contaminated with impurities may be treated with dimethyl sulfoxide to form selectively the dimethyl sulfoxide adduct of the sodium salt of Penicillin I or II, which is highly crystallizable. For instance, the sodium salt of Penicillin I or II in a crude state is contacted with or dissolved in a dimethyl sulfoxide-containing liquid medium, and the deposited crystals of the dimethyl sulfoxide adduct of the sodium salt of Penicillin I or II is collected by a conventional separation procedure. If, the collected dimethyl sulfoxide adduct may be dissolved in a water-containing liquid medium, followed by addition of an appropriate solvent, in which the sodium salt of Penicillin I or II is weakly soluble, to deposit the sodium salt of Penicillin I or II as crystals. The dimethyl sulfoxide adduct of the sodium salt of Penicillin I or II and the sodium salt of Penicillin I or II as above obtained are of high purity.

As the dimethyl sulfoxide-containing liquid medium, there may be used dimethyl sulfoxide alone or a mixture of dimethyl sulfoxide with any other suitable organic solvent such as an alcoholic solvent (e.g. methanol, ethanol, isopropanol), acetonitrile, acetone or a hydrocarbon solvent (e.g. benzene, toluene, hexane). Depending on the case, these suitable organic solvents may be used in combination. Further, water may be included in the dimethyl sulfoxide-containing liquid medium. Preferred is a mixture of dimethyl sulfoxide and an alcoholic solvent.

As the water-containing liquid medium, there may be used a mixture of water and one or more polar solvents such as alcoholic solvents (e.g. methanol, ethanol, isopropanol), dioxane, tetrahydrofuran, dimethylformamide, acetonitrile and acetone. Preferable is a mixture of water and an alcoholic solvent, particularly methanol. Although no limitation is present on the water content, lower is usually better.

Examples of the solvent suitable for deposition of the liberated sodium salt of Penicillin I or II are acetone, acetonitrile, isopropanol, ether, isopropyl ether, tetrahydrofuran, dichloromethane, etc.

On the formation of the dimethyl sulfoxide adduct, the temperature is not particularly limitative. But, room temperature (about 5° to 20° C.) to about 60° C. is usually favorable. When the temperature is higher than about 60° C., the sodium salt of Penicillin I or II is apt to be decomposed, and the yield of the dimethyl sulfoxide adduct is lowered. When the temperature is lower than room temperature, the formation of the dimethyl sulfoxide adduct becomes difficult. The reaction time may be within 24 hours, normally from 1 to 2 hours.

For the decomposition of the dimethyl sulfoxide adduct, no particular limitation exists on the temperature, and the performance at room temperature (about 5° to 20° C.) or lower is usually preferable. The time may be from 20 to 60 minutes, usually about 30 minutes, after the dimethyl sulfoxide adduct is dissolved.

The sodium salt of Penicillin I or II, from which the dimethyl sulfoxide adduct should be formed, may be formed in situ on treatment with the dimethyl sulfoxide-containing liquid medium. For instance, Penicillin I or II or its ammonium or amine salt is treated with sodium or its compound in the dimethyl sulfoxide-containing liquid medium, whereby the dimethyl sulfoxide adduct of the sodium salt of Penicillin I or II is formed and deposited as crystals. Examples of the ammonium or amine salt include ammonium, triethylamine, tri-n-butylamine, dibenzylamine, N-benzyl-β-phenethylamine, 1-ephenamine, N,N'-dibenzylethylenediamine, procaine, dehydroabiethylethylenediamine and arginine salts. As the sodium compound, there may be exemplified sodium hydroxide, sodium carbonate, sodium hydrogencarbonate, sodium acetate, sodium 2-ethylhexanoate, sodium methoxide, sodium ethoxide, sodium phenoxide, sodium thiocyanate, acetylacetonatosodium, etc. In general, the sodium salt of a carboxylic acid such as sodium 2-ethylhexanoate is preferably employed.

The solution of the dimethyl sulfoxide adduct may be adjusted to an appropriate pH prior to its decomposition for liberation of dimethyl sulfoxide therefrom, if necessary. In such case, the pH adjustment is ordinarily carried out by the use of the sodium compound as exemplified above.

Practical and presently preferred embodiments of the present invention are illustratively shown in the following Examples wherein the purity (% by weight) was determined by high performance liquid chromatography.

REFERENCE EXAMPLE 1

(1) Preparation of N-(4-hydroxy-1,5-naphthyridine-3-carbonyloxy)succinimide:

To a solution of dimethylformamide (47.5 kg) containing pyridine (4.7 kg), there were added 4-hydroxy-1,5-naphthyridine-3-carboxylic acid (2.8 kg) and N-hydroxy-succinimide (2.2 kg). To the mixture, there was dropwise added thionyl chloride (2.1 kg) while stirring at room temperature, and stirring was continued for 5 hours at the same temperature. The precipitated crystals were collected by filtration, washed with acetone and dried under reduced pressure to give 4.3 kg of N-(4-hydroxy-1,5-naphthyridine-3-carbonyloxy)succinimide. Purity, 97%

(2) Preparation of sodium 6-[D(−)-α-(4-hydroxy-1,5-naphthyridine-3-carboxamido)phenylacetoamido]-penicillanate:

To a solution of triethylamine (2.5 kg) in dimethyl sulfoxide (18.0 kg), there were added ampicillin trihydrate (5.0 kg) and N-(4-hydroxy-1,5-naphthyridine-3-carbonyloxy)succinimide (3.45 kg). After stirring at room temperature, acetone (64 kg) was poured into the reaction mixture. Precipitated white crystals were collected by filtration, washed with acetone and dried under reduced pressure to give the triethylamine salt of 6-[D(−)-α-(4-hydroxy-1,5-naphthyridine-3-carboxamido)phenylacetamido]-penicillanic acid.

The triethylamine salt so obtained was dissolved at room temperature in a mixture of dimethyl sulfoxide (7.8 kg) and methanol containing sodium 2-ethylhexanoate (2.4 kg) under stirring over 30 minutes. Acetone (94 kg) was then poured into the reaction mixture, and precipitated white crystals were collected by filtration and washed with acetone. The wet cake so obtained was dissolved in methanol (16 kg) and, after removal of insoluble materials by filtration with celite, acetone (94 kg) was added to the filtrate. Precipitated white crystals were collected by filtration, washed with acetone and dried under reduced pressure to give 5.3 kg of sodium 6-[D(−)-α-(4-hydroxy-1,5-naphthyridine-3-carboxamido)phenylacetamido]penicillanate. Purity, 95.5%.

EXAMPLE 1

Crude sodium 6-[D(−)-α-(4-hydroxy-1,5-naphthyridine-3-carboxamido)phenylacetamido]penicillanate (5.0 kg; purity, 95.5%) was dissolved in a mixture of dimethyl sulfoxide (10.1 kg) and methanol (6.2 kg) at room temperature. Thereafter, the temperature of the mixture was elevated, and stirring was continued at 50° to 55° C. for one hour. Precipitated white crystals were collected by filtration and washed with a mixture of dimethyl sulfoxide (1.0 kg) and methanol (0.6 kg). The crystals were further washed with acetone (16 kg) and dried to give 4.2 kg of the dimethyl sulfoxide adduct of sodium 6-[D(−)-α-(4-hydroxy-1,5-naphthyridine-3-carboxamido)phenylacetamido]penicillanate. Purity, 99.5%.

The dimethyl sulfoxide adduct (4 kg) so obtained was dissolved in 93% aqueous methanol (10.8 kg). To the methanol solution, acetone (84 kg) was dropwise added. The precipitated white crystals were collected by filtration, washed with acetone (14 kg) and dried to give 3.5 kg of sodium 6-[D(−)-α-(4-hydroxy-1,5-naphthyridine-3-carboxamido)phenylacetamido]penicillanate. Purity 99.2%.

EXAMPLE 2

In a mixture of dimethyl sulfoxide (13 kg) and methanol (8 kg), there was dissolved at room temperature 6.4 kg of crude sodium 6-[D(−)-α-(4-hydroxy-1,5-naphthyridine-3-carboxamido)phenylacetamido]penicillanate (purity, 92.0%) containing the β-lactam ring cleaved decomposition substance. The resultant mixture was heated and stirred at 50° to 55° C. for one hour. Precipitated white crystals were filtered and washed with a mixture of dimethyl sulfoxide (1.3 kg) and methanol (0.8 kg). Thereafter, the crystals were further washed with acetone (20 kg) and dried to give 5.3 kg of the dimethyl sulfoxide adduct of 6-[D(−)-α-(4-hydroxy-1,5-naphthyridine-3-carboxamido)-phenylacetamido]penicillanate. Purity, 99.3%. M.P. 265°–270° C. (decomp.).

| Analysis for $C_{27}H_{28}O_7N_5S_2Na$: | | |
|---|---|---|
| | Calcd. (%) | Found (%) |
| C | 52.2 | 52.0 |
| H | 4.5 | 4.5 |
| N | 11.3 | 11.2 |
| S | 10.3 | 10.5 |

The dimethyl sulfoxide adduct (5 kg) so obtained was dissolved in 93% aqueous methanol (13.5 kg), and thereafter acetone (105 kg) was dropwise added to the resultant solution to precipitate crystals. The precipitated white crystals were collected by filtration, washed with acetone (17 kg) and dried to give 4.3 kg of sodium 6-[D(−)-α-(4-hydroxy-1,5-naphthyridine-3-carboxamido)phenylacetamido]penicillanate. Purity, 99.0%.

EXAMPLE 3

In a mixture of dimethyl sulfoxide (13 kg) containing sodium 2-ethylhexanoate (2 kg) and methanol (8 kg), there was dissolved 7.1 kg of the triethylamine salt of 6-[D(−)-α-(4-hydroxy-1,5-naphthyridine-3-carboxamido)phenylacetamido]penicillanic acid (purity, 98.5%). The resultant mixture was heated and stirred at 50° to 55° C. for one hour. Precipitated white crystals were collected by filtration and washed with a mixture of dimethyl sulfoxide (1.3 kg) and methanol (0.8 kg). The crystals were further washed with acetone (20 kg) and dried to give 5.2 kg of the dimethyl sulfoxide adduct of sodium 6-[D(—)-α-(4-hydroxy-1,5-naphthyridine-3-carboxamido)phenylacetamido]penicillanate. Purity, 99.1%.

The dimethyl sulfoxide adduct (5 kg) was dissolved in 93% aqueous methanol (13.5 kg), and acetone (105 kg) was dropwise added to the resultant solution to precipitate crystals. The precipitated white crystals were collected by filtration, washed with acetone (17 kg) and dried to give 4.2 kg of sodium 6-[D(—)-α-(4-hydroxy-1,5-naphthyridine-3-carboxamido)phenylacetamido]penicillanate. Purity, 98.8%.

EXAMPLE 4

In a mixture of dimethyl sulfoxide (13 kg) and methanol (8 kg), there was dissolved at room temperature 6.4 kg of crude sodium 6-[D(—)-α-(4-hydroxy-1,5-naphthyridine-3-carboxamido)phenylacetamido]penicillanate containing its optical isomer at the phenylglycine portion (L-isomer content, 0.2%). The resultant mixture was heated and stirred at 50° to 55° C. for one hour. Precipitated white crystals were collected by filtration and washed with a mixture of dimethyl sulfoxide (1.3 kg) and methanol (0.8 kg). The crystals were further washed with acetone (20 kg) and dried to give 5.2 kg of the dimethyl sulfoxide adduct of sodium 6-[D(—)-α-(4-hydroxy-1,5-naphthyridine-3-carboxamido)-phenylacetamido]penicillanate.

The dimethyl sulfoxide adduct (5 kg) was dissolved in 93% aqueous methanol (13.5 kg), and acetone (105 kg) was dropwise added to the resultant solution to precipitate crystals. The precipitated white crystals were collected by filtration and washed with a mixture of dimethyl sulfoxide (1.3 kg) and methanol (0.8 kg). Thereafter, the crystals were further washed with acetone (20 kg) and dried to give 4.2 kg of sodium 6-[D(—)-α-(4-hydroxy-1,5-naphthyridine-3-carboxamido)-phenylacetamido]penicillanate. L-isomer content, less than 0.05%.

EXAMPLE 5

In a mixture of dimethyl sulfoxide (13 kg) and methanol (8 kg), there was dissolved at room temperature 6.4 kg of sodium 6-[D,L-α-(4-hydroxy-1,5-naphthyridine-3-carboxamido)phenylacetamido]penicillanate containing its optical isomer (L-isomer content, 49.5%). The resultant mixture was heated and stirred at 50° to 55° C. for one hour. Precipitated white crystals were collected by filtration and washed with a mixture of dimethyl sulfoxide (1.3 kg) and methanol (0.8 kg). The crystals were further washed with acetone (20 kg) and dried to give 2.1 kg of the dimethyl sulfoxide adduct of sodium 6-[D(—)-α-(4-hydroxy-1,5-naphthyridine-3-carboxamido)phenylacetamido]penicillanate. L-isomer content, 0.1%.

The dimethyl sulfoxide adduct (2 kg) obtained above was dissolved in 93% aqueous methanol (5.5 kg), and acetone (50 kg) was dropwise added to the resultant solution. The precipitated white crystals were collected by filtration, washed with acetone (8 kg) and dried to give 1.7 kg of sodium 6-[D(—)-α-(4-hydroxy-1,5-naphthyridine-3-carboxamido)phenylacetamido]penicillanate. L-isomer content, 0.1%.

EXAMPLE 6

In a mixture of dimethyl sulfoxide (27 kg) and methanol (16.5 kg), there was dissolved at room temperature 14.3 kg of crude sodium 6-[D(—)-α-(4-hydroxy-1,5-naphthyridine-3-carboxamido)-p-hydroxyphenylacetamido]penicillanate containing the β-lactam ring cleavage decomposition substance (purity, 96.0%). The resultant mixture was stirred at room temperature for one hour. Precipitated white crystals were collected by filtration and washed with a mixture of dimethyl sulfoxide (2.7 kg) and methanol (1.7 kg). The crystals were further washed with acetone (40 kg) and dried to give 8.0 kg of sodium 6-[D(—)-α-(4-hydroxy-1,5-naphthyridine-3-carboxamido)-p-hydroxyphenylacetamido]penicillanate. Purity, 99.6%. M.P. 275°–280° C. (decomp.).

| Analysis for $C_{27}H_{28}O_8N_5S_2Na$: | | |
|---|---|---|
| | Calcd. (%) | Found (%) |
| C | 50.9 | 51.0 |
| H | 4.4 | 4.4 |
| N | 11.0 | 11.2 |
| S | 10.1 | 10.3 |

The dimethyl sulfoxide adduct (8 kg) obtained above was dissolved in 93% aqueous methanol (22 kg), and acetone (170 kg) was dropwise added to the resultant solution. The precipitated white crystals were collected by filtration, washed with acetone (27 kg) and dried to give 7.5 kg of sodium 6-[D(—)-α-(4-hydroxy-1,5-naphthyridine-3-carboxamido)-p-hydroxyphenylacetamido]penicillanate. Purity, 98.8%.

EXAMPLE 7

In a mixture of dimethyl sulfoxide (27 kg) containing 4 kg of sodium 2-ethylhexanoate and methanol (16.5 kg), there was dissolved 15.1 kg of the triethylamine salt of 6-[D(—)-α-(4-hydroxy-1,5-naphthyridine-3-carboxamido)-p-hydroxyphenylacetamido]penicillanic acid (purity, 98.4%). The resultant reaction mixture was stirred at room temperature for one hour. Precipitated white crystals were collected by filtration and washed with a mixture of dimethyl sulfoxide (2.7 kg) and methanol (1.7 kg). The crystals were further washed with acetone (40 kg) and dried to give 7.8 kg of dimethyl sulfoxide adduct of sodium 6-[D(—)-α-(4-hydroxy-1,5-naphthyridine-3-carboxamido)-p-hydroxyphenylacetamido]-penicillanate. Purity, 99.5%.

The dimethyl sulfoxide adduct (7.5 kg) obtained above was dissolved in 93% aqueous methanol (20 kg), and acetone (160 kg) was dropwise added to the resultant solution. The precipitated white crystals were collected by filtration, washed with acetone (25 kg) and dried to give 7 kg of sodium 6-[D(—)-α-(4-hydroxy-1,5-naphthyridine-3-carboxamido)-p-hydroxyphenylacetamido]penicillanate. Purity, 98.6%.

EXAMPLE 8

In a mixture of dimethyl sulfoxide (13 kg) and methanol (8 kg), there was dissolved at room temperature 6.5 kg of sodium 6-[D,L-α-(4-hydroxy-1,5-naphthyridine-3-carboxamido)-p-hydroxyphenylacetamido]penicillanate containing its optical isomer (L-isomer content, 50.1%). The resultant mixture was stirred at room temperature for one hour. Precipitated white crystals were collected by filtration and washed with a mixture of dimethyl sulfoxide (1.3 kg) and methanol (0.8 kg). The crystals were further washed with acetone (20 kg) and dried to give 1.8 kg of the dimethyl sulfoxide adduct of sodium 6-[D(−)-α-(4-hydroxy-1,5-naphthyridine-3-carboxamido)-p-hydroxyphenylacetamido]penicillanate. L-isomer content, 0.1%.

The dimethyl sulfoxide adduct (1.8 kg) obtained above was dissolved in 93% aqueous methanol (5 kg), and acetone (50 kg) was dropwise added to the resultant solution. The precipitated white crystals were collected by filtration, washed with acetone (8 kg) and dried to give 1.4 kg of sodium 6-[D(−)-α-(4-hydroxy-1,5-naphthyridine-3-carboxamido)-p-hydroxyphenylacetamido]-penicillanate. Purity, 98.6%. L-isomer content, 0.1%.

What is claimed is:

1. A dimethyl sulfoxide adduct of sodium 6-[D(−)-α-(4-hydroxy-1,5-naphthyridine-3-carboxamido)-phenylacetamido]penicillanate or its hydroxylated derivative at the p-position of the phenyl group.

2. A process for preparing the dimethyl sulfoxide adduct according to claim 1, which comprises reacting sodium 6-[D(−)-α-(4-hydroxy-1,5-naphthyridine-3-carboxamido)-phenylacetamido]penicillinate or its hydroxylated derivative at the p-position of the phenyl group and dimethyl sulfoxide in an organic solvent selected from the group consisting of an alcoholic solvent, acetonitrile, acetone and a hydrocarbon solvent at about 5° to 60° C.

3. The process according to claim 2, wherein the sodium 6-[D(−)-α-(4-hydroxy-1,5-naphthyridine-3-carboxamido)phenylacetamido]penicillanate or its hydroxylated derivative at the p-position of the phenyl group is present in a crude state.

4. The process according to claim 2, wherein the sodium 6-[D(−)-α-(4-hydroxy-1,5-naphthyridine-3-carboxamido)-phenylacetamido]penicillante or its hydroxylated derivative at the p-position of the phenyl group is formed in situ.

5. The process according to claim 4, wherein the sodium 6-[D(−)-α-(4-hydroxy-1,5-naphthyridine-3-carboxamido)phenylacetoamido]penicillanate or its hydroxylated derivative at the p-position of the phenyl group is formed in situ from the corresponding free acid or its ammonium or amine salt and sodium or its compound.

6. A process for decomposing the dimethyl sulfoxide adduct according to claim 1, which comprises: dissolving the dimethyl sulfoxide adduct in a mixture of water and one or more polar solvents so as to liberate sodium 6-[D(−)-α-(4-hydroxy-1,5-naphthyridine-3-carboxamido)phenylacetamido]penicillinate or its hydroxylated derivative at the p-position of the phenyl group and dimethyl sulfoxide adduct.

7. A process for purification of crude sodium 6-[D(−)-α-(4-hydroxy-1,5-naphthyridine-3-carboxamido)phenylacetamido]penicillinate or its hydroxylated derivative at the p-position of the phenyl group, which comprises: reacting the sodium salt with dimethyl sulfoxide in a liquid medium to deposit the dimethyl sulfoxide adduct of the sodium salt, collecting the deposited dimethyl sulfoxide adduct, dissolving the collected dimethyl sulfoxide adduct in a mixture of water and one or more polar solvents to liberate the sodium salt and dimethyl sulfoxide, adding thereto a solvent in which the sodium salt is weakly soluble and collecting the deposited sodium salt.

8. A process according to claims 6 or 7 wherein the polar solvents are alcoholic solvents.

* * * * *

UNITED STATES PATENT AND TRADEMARK OFFICE
CERTIFICATE OF CORRECTION

PATENT NO. : 4,244,870
DATED : January 13, 1981
INVENTOR(S) : Norihiko TANNO et al It is certified that error appears in the above—identified patent and that said Letters Patent is hereby corrected as shown below:

In column 6, line 14, after "8.0 kg of" insert --the dimethyl sulfoxide adduct of--.

Signed and Sealed this

Twenty-ninth Day of September 1981

[SEAL]

Attest:

GERALD J. MOSSINGHOFF

Attesting Officer

Commissioner of Patents and Trademarks